United States Patent [19]
Stachecki

[11] Patent Number: 5,985,538
[45] Date of Patent: Nov. 16, 1999

[54] CRYOPRESERVATION AND CELL CULTURE MEDIUM COMPRISING LESS THAN 50 MM SODIUM IONS AND GREATER THAN 100 MM CHOLINE SALT

[75] Inventor: James J. Stachecki, Parsippany, N.J.

[73] Assignee: Saint Barnabas Medical Center, Livingston, N.J.

[21] Appl. No.: 08/904,671

[22] Filed: Aug. 1, 1997

[51] Int. Cl.$^6$ .................................................. A01N 1/02
[52] U.S. Cl. ................................ 435/1.1; 435/1.3; 435/2
[58] Field of Search ................................ 435/1.1, 1.3, 2

[56] References Cited

U.S. PATENT DOCUMENTS

| | | | |
|---|---|---|---|
| 4,965,185 | 10/1990 | Grischenko et al. | 435/2 |
| 4,965,186 | 10/1990 | Grischenko et al. | 435/2 |
| 5,084,377 | 1/1992 | Rowan et al. | 435/1 |
| 5,250,303 | 10/1993 | Meryman et al. | 424/533 |
| 5,795,771 | 8/1998 | George et al. | 435/255.21 |

OTHER PUBLICATIONS

Chen et al., "Effect of Sucrose, Trehalose, Hypotaurine, Taurine and Blood Serum on Survival of Frozen Bull Sperm", Cryobiology 30 (4) 423:31 (1993).
Billard et al., "Motility of Fresh and Aged Halibut Sperm", Aquatic Living Resources 6(1): 67–75 (1993).
Bhela et al., "Effect of Buffers on Motility, Livability and Metabolism of Buffalo Spermatozoa", Indian J. Animal Sci. 51 (10): 926–30 (1981).
ATCC Catalogue of Bacteria & Bacteriophages, p. 443, entry 778, 1992.
Gibco Catalogue, p. 112, 1992.
Sucher et al., Neuroscience 43(1): 135–50 (1991).
Aigner, S. et al, (1992). The Influence of slow and ultra–rapid freezing on the organization of the meiotic spindle of the mouse oocyte. Human Reproduction 7, 857–64.
AL–Hasani et al. (1987). Cryopreservation of human oocytes. Human Reproduction 2, 695–700.
Bouquet M, et al. (1992). The incidence of chromosomal abnormalities in frozen–thawed mouse oocytes after in–vitro fertilization. Human Reproduction 7, 76–80.
Carroll, J. et al. (1989). Increase in digyny explains polyploidy after in–vitro fertilization of frozen–thawed mouse oocytes. Journal of Reproduction & Fertility 85, 489–94.
Carroll, J. et al. (1990). Freeze–thaw–induced changes of the zona pellucida explains decreased rates of fertilization in frozen–thawed mouse oocytes. Journal of Reproduction & Fertility 90, 547–53.
Carroll, J, et al, (1993), Normal fertilization and development of frozen–thawed mouse oocytes: protective action of certain macromolecules. Biology of Reproduction 48, 606–12.
Chatot, Cl., et al. (1989). An improved culture medium supports development of randon–bred 1–cell mouse embryos in vitro. Journal of Reproduction & Fertility 86, 679–88.

Chen, C. (1986). Pregnancy after human oocyte pricryopreservation. Lancet 1, 884–6.
Cohen, J. et al. (1988). Duration of storage of cryopreserved human embryos. Journal of in Vitro Fertilization & Embryo Transfer 5, 301–3.
Friedler, S. et al. (1988). Cryopreservation of Embryos and ova. Fertility & Sterility 49, 743–64.
Fuku, E. et al. (1992). In vitro fertilization and development of frozen–thawed bovine oocytes. Cryobiology 29, 485–92.
George, Ma et al. (1993). Use of fetal bovine serum substitutes for the protection of the mouse zona pellucida against hardening during cryoprotectant addition. Human Reproduction 8, 1898–900.
George, Ma et al. (1994). Assessment of the development potential of frozen–thawed mouse oocytes. Human Reproduction 9, 130–6.
Glenister, P.H. et al. (1987). Incidence of chromosome anomalies in first–cleavage mouse embryos obtained from frozen–thawed oocytes fertilized in vitro. Gamete Research 16, 205–16.
Gook, D.A. et al. (1993). Cryoperservation of mouse and human oocytes using 1,2–propanediol and the configuration of the meiotic spindle. Human Reproduction 8, 1101–9.
Gook, D.A. et al. (1995). Intracytoplasmic sperm injection and embryo development of human oocytes cryopreserved using 1,2–propanediol. Human Reproduction 10, 2637–41.
Imoedemhe, D.G. et al. (1992). Survival of human oocytes cryopreserved with or without the cumulus in 1,2–propanediol. Journal of Assisted Reproduction & Genetics 9, 323–7.
Kasai, K. et al. (1981). Observations on the chromosome number in the first and the second cleavage division of mouse embryos derived from fertilization in vitro. Kitasato Archives of Experimental Medicine 54, 17–24.
Kimura, Y. et al. (1995). Intracytoplasmic sperm injection in the mouse. Biology of Reproduction 52, 709–20.
Lassalle, B. et al. (1985). Human embryo features that influence the success of cryopreservation with the use of 1,2 propanediol. Fertility & Sterility 44, 645–51.
Lovelock, J. E. (1954). The protective action of neutral solutes against haemolysis by freezing and thawing Biochemistry Journal 56, 265.
Mandelbaum, J. et al. (1987). Human embryo cryopreservation, extrinsic and intrinsic parameters of success. Human Reproduction 2, 709–15.

(List continued on next page.)

*Primary Examiner*—Sandra E. Saucier
*Attorney, Agent, or Firm*—Milde, Hoffberg & Macklin, LLP

[57] ABSTRACT

A cell culture medium and cryopreservation medium in which sodium chloride is replaced with an organic cation, preferably choline chloride in a concentration of at least 100 mM, resulting a residual sodium ion concentration less than about 50 mM. The cryopreservation solution is suitable for cryopreservation of unfertilized oocytes, with thawed oocytes demonstrating the ability to survive, fertilize, and for the resulting embryos to proceed to full term development.

49 Claims, No Drawings

OTHER PUBLICATIONS

Mazur, P. (1977). The role of intracellular freezing in the death of cells cooled at supraoptimal rates. Cryobiology 14, 251–72.

Mazur, P. et al. (1974). Survival of frozen–thawed bovine red cells as a function of the permeation of glycerol and sucrose. Journal of Membrane Biology 15, 137–58.

Renard, J.P. et al. (1984). Two–step freezing of two–cell rabbit embryos after partial dehydration at room temperature. Journal of Reproduction & Fertility 71, 573–80.

Schroeder, A.C. et al. (1990). Developmental capacity of mouse oocytes cryopreserved before and after maturation in vitro. Journal of Reproduction & Fertility 89, 43–50.

Shaw, J.M. et al. (1995). Evaluation of propanediol, ethylene glycol, sucrose and antifreeze proteins on the survival of slow–cooled mouse pronuclear and 4–cell embryos. Human Reproduction 10, 396–402.

Testart, J. et al. (1986). Cryopreservation does not affect future of human fertilized eggs. Lancet 2, 569.

Todorow, S.J. et al. (1989). Comparative results on survival of human and animal eggs using different cryoprotectants and freeze–thawing regimens II. Human Reproduction 4, 812–6.

Toner, M. et al. (1991). Cryomicroscopic analysis of intracellular ice formation during freezing of mouse oocytes without cryoadditives. Cryobiology 28, 55–71.

Toner, M. et al. (1993). Nonequilibrium freezing of one–cell mouse embryos. Membrane integrity and developmental potential. Biophysical Journal 64, 1908–21.

Vincent, C. et al. (1990). The hardening effect of dimethyl-sulphoxide on the mouse zona pellucida requires the presence of an oocyte and is associated with a reduction in the number of cortical granules present. Journal of Reproduction & Fertility 89, 253–9.

Whittingham, D.G. et al. (1972). Survival of mouse embryos frozen to–196 degrees and –269 degrees C. Science 178, 411–4.

Whittingham, D.G. et al. (1977). Long–term storage of mouse embryos at—196 degrees C: the effect of background radiation. Genetical Research 29, 171–81.

Willadsen, S. et al. (1976). Deep freezing of sheep embryos. Journal of Reproduction & Fertility 46, 151–4.

Willadsen, S.M. (1977). Factors affecting the survival of sheep embryos during freezing and thawing. Ciba Foundation Symposium, 175–201.

Willadsen, S. et al. (1978). The viability of deep–frozen cow embryos. Journal of Reproduction & Fertility 52, 391–3.

Glenister, P.H. et al. (1990). Genome cryopreservation: a valuable contribution to mammalian genetic research. Genetical Research 56, 253–8.

CRYOPRESERVATION AND CELL CULTURE MEDIUM COMPRISING LESS THAN 50 MM SODIUM IONS AND GREATER THAN 100 MM CHOLINE SALT

FIELD OF THE INVENTION

This invention relates to culture medium, specifically to an improved culture medium suitable for incubation and cryopreservation of cells.

BACKGROUND OF THE INVENTION

The ability to cryopreserve mammalian oocytes with high success rates in an easily reproducible manner has not yet been achieved. Cryopreservation of mouse oocytes, for example, could be valuable for the long term storage of genetically important strains of mice and would serve as a model for oocyte cryopreservation in humans, commercial livestock, and endangered species. This technology could also help alleviate the legal, ethical, and religious problems associated with the storage of human embryos, as well as improve current embryo freezing protocols. Although offspring have been produced from frozen-thawed oocytes in the mouse, human, bovine, and rabbit (Whittingham, 1977; Al-Hasani et al., 1987; Fuku et al., 1992; Chen 1986; Van Uem et al., 1987), results have been variable and not sufficiently successful to make oocyte cryopreservation routine.

In addition to oocyte freezing, cryopreservation and transplantation of ovarian autografts have been somewhat successful in mice and sheep (Gosden et al., 1994; Gunasena et al., 1997). The ovarian tissues in these reports were frozen using simple embryo freezing protocols. Ovarian tissue survived freezing and was able to continue development after transplantation to the reproductive tract or kidney capsule, yielding growing follicles.

Current cryopreservation protocols have evolved from embryo freezing methods that produced offspring in mice, cows, and sheep (Whittingham et al., 1972; Willadsen et al., 1976, 1978). Cryopreservation procedures for mouse and other mammalian embryos are now relatively efficient, but these techniques cannot be used reliably for oocyte freezing. Studies cryopreserving mouse oocytes report very different survival and fertilization rates (Carroll et al., 1993; Carroll et al., 1990; Cohen et al., 1988; George et al., 1994; Glenister et al., 1990; Gook et al., 1993; Whittingham et al., 1977). The variability in the success of mouse oocyte freezing is most likely due to modifications in freezing protocol and/or the use of different cryoprotectants. Although these protocols differ, they rely on the same basic cryobiological principals.

A particularly important area that would benefit greatly from advances in cryopreservation technology is assisted human reproduction. In this field, one or both partners may have a fertility problem. In order to overcome these problems, eggs are harvested from the mother, and sperm from the father. The sperm are then used to fertilize the eggs, and one or more developing embryos are then replaced to the uterus of the mother. Typically, egg maturation is induced pharmaceutically prior to harvesting, and the sperm must be available to fertilize the eggs. Generally, only a very limited number of surgical harvesting procedures may be conducted on an individual, and the number of eggs replaced in the mother is limited in order to avoid multiple live births. Therefore, there has been a need to preserve harvested eggs, sperm, fertilized eggs, and embryos.

The ability to successfully and reproducibly cryopreserve oocytes, which is not yet possible, would allow women to have their eggs frozen until a time when they have found a suitable sperm donor (possibly a future husband) and then thaw their frozen eggs and fertilize them. The resulting embryos can be replaced into the patients' uterus, after it has been prepared to receive the embryo using hormones and known techniques, to allow for implantation, fetal development, and ultimately birth. Ethically, there are issues involved in preserving fertilized eggs or embryos, that are more significant than those associated with freezing unfertilized germ cells. Cryopreservation of oocytes would avoid the ethical concerns surrounding embryo freezing in humans and offer another option to couples with infertility problems. Storing oocytes early in life, such as when the mother is in her 20's and early 30's, when healthy eggs tend to be produced, and therefore when they are more apt to be fertilized and result in viable offspring, would greatly improve the chance of a pregnancy later in life, rather than the relatively poor pregnancy rates produced when participating in an in vitro fertilization (IVF) program at 40 years old or older.

Cryopreservation of oocytes, especially from humans, in a reproducible and efficient manner has been generally unsuccessful according to known techniques. It is noted, however, that offspring have been produced from frozen oocytes of several species, including humans. An improved cryopreservation medium would benefit oocyte storage and may also provide a more successful way of freezing embryos, thereby improving the possibilities for pregnancy.

Cryopreservation technology is applicable to other species besides humans. In commercial livestock, improvements in oocyte or embryo cryopreservation could greatly improve genetic management of populations and the number of offspring generated, resulting in a significant time savings and efficiency. In endangered animals, any improvement in embryo freezing or the development of a method to freeze eggs could lead to an increase in the number of offspring produced, enhancement of the genetic quality of the offspring, improvement of the population's genetic health, elimination of both the cost and risk of transporting live animals for reproductive purposes, and possibly even a delay or prevention from extinction of certain species.

Cryopreservation of oocytes from commercial livestock would provide a valuable means of saving and distributing important genetic material. Oocytes from animals exhibiting commercially valuable traits such as increased milk production could be stored.

Cryopreservation of oocytes from endangered species would provide an invaluable method of salvaging important genetic material. Provided that the eggs could be thawed, fertilized, and produce fertile offspring, and given that sperm is relatively easy to store, species could be stored indefinitely, virtually eliminating the risk of extinction. Cryopreserved oocytes could be easily transported globally, providing a source of genetic information to better aid in managing populations. In this manner, underrepresented genes from founder animals could be reintroduced into the population at any time, even 200 years from now. Because frozen oocytes (and sperm) can be distributed easily and cost effectively, the possibilities of improving genetic diversity and the overall health of a population are intriguing. Oocytes collected in the field can be frozen and infused into the captive population to improve its genetic health. With this technology in place frozen zoos can become a reality.

Biological cryopreservation systems are well known. They allow cells to be frozen, for example at −20° C. or below, for extended periods, and resume normal cell activity after thawing. Typically, problems encountered include intracellular ice formation (IIF) and osmotic imbalances that result in cellular disruption. It is the prevention of IIF that many prior methods are directed.

Cryopreservation of cells involves dehydration, introduction of a cryoprotectant, and cooling to a low temperature, usually from −30° C. to −80° C., before plunging in $LN_2$. The first objective is the removal of water from the cell, which when cooled below its melting point forms ice crystals that can damage intracellular organelles as well as the cell membrane (Mazur, 1977). The osmolality of the extracellular solution increases as the outside water freezes, causing the water to passively exit the cell. More ice forms at lower temperatures resulting in continued cellular dehydration. The next objective for freezing cells concerns the combining of any residual water left in the cell with a cryoprotectant, in order to form a glass-like structure when solidified, thereby preventing IIF. Because the melting point of water is reached both during freezing and thawing, IIF can occur at either time. Damage may therefore occur when the cell is exposed to elevated concentrations of electrolytes and/or IIF. IIF can be catalyzed by the presence of extracellular ice surrounding the cells (seeding) or heterogeneously by intracellular structures. In the presence of cryoprotectants however, IIF resulting from either seeding and/or heterogeneous ice nucleation does not occur (Toner et al., 1991), suggesting that IIF may not be a problem when freezing oocytes in the presence of a cryoprotectant. Therefore, electrolytes including sodium would appear to impart the majority of the damage during cryopreservation. Cellular disruption by sodium ions could alter the cell membrane and/or intracellular organelles. Lovelock (1954) hypothesized that cellular damage is caused by an increase in electrolyte concentration, causing destabilization of membranes. Mazur et al. (1974) further demonstrated that the cell surface is a major site of freezing damage. In his study, Mazur showed that the nonpermeating solute sucrose was as effective in protecting erythrocytes from freeze/thaw damage as the permeable cryoprotectant glycerol. The majority of damage to mouse oocytes during freezing may be caused by sodium ions, but we cannot rule out the possibility of IIF. Whether cellular demise is caused by exposure to elevated sodium ion concentrations during the freeze or thaw, or a problem with the transport of sodium ions across cell membranes remains to be elucidated. Sodium ions have a radius of about 0.95 Å, while lithium has a radius of 0.60 Å and potassium has a radius of about 1.33 Å. The majority of past cryopreservation studies that have focused on IIF, cryoprotectants, and altering freezing protocols have been unable to significantly improve oocyte freezing. Therefore, the type of cryoprotectant used, or the freezing protocol may already be adequate for oocyte freezing and IIF may not be the major problem presumed by the prior art.

Standard embryo cryopreservation techniques are remarkably similar. In general, embryos are exposed to a cryoprotectant (dimethyl sulfoxide (DMSO), 1,2-propanediol (PrOH), glycerol, ethylene glycol), diluted in a simple sodium-based salt solution for 5–15 min to allow uptake of the cryoprotectant. The embryos are then cooled quickly (−2° C./min) to about 7° C. at which point they are seeded, cooled slowly (−0.3° C. to −0.5° C./min) to about −30° C. or below, and then plunged directly into liquid nitrogen ($LN_2$). Embryos can also be rapidly frozen or vitrified, but only using very elevated cryopreservative concentrations (2M to 6M) that are toxic to cells when they are exposed for more than a few minutes. Following cryopreservation the embryos are thawed and cultured. Thawing procedures differ, but very little. Two basic concepts are involved in the thawing process, 1) removal of cryoprotectant and 2) rehydration of the embryo at a rate so as not to rupture the cell membrane, usually with the use of sucrose. These freezing and thawing procedures work relatively well for embryos, but do not allow the successful storage of oocytes. The exact reason(s) why embryos can survive and oocytes cannot are unknown, but membrane damage due to IIF, ion loading, and/or osmotic stress are suspect. Researchers have mainly focused on the problem of IIF and osmotic stress by modifying freezing procedures (slow vs. fast), thawing procedures (slow vs. fast), and methods for the removal of the cryoprotectants with little attention to the cryopreservation media formulation, which is presumed to be optimal.

Researchers have tried unsuccessfully to cryopreserve oocytes in a reproducible manner using one or more cryoprotectants. In general, PrOH and DMSO are the most common cryoprotectants used today for the cryopreservation of oocytes and embryos. Although all of the pregnancies in the human have resulted from oocytes frozen in DMSO, PrOH is the cryoprotectant of choice because of its greater permeability, reduced toxicity, and improved success in storing human embryos (Gook et al., 1995; Imoedemhe and Sigue, 1992; Lassalle et al., 1985; Mandelbaum et al., 1987; Testart et al., 1986). Mouse oocytes have been frozen using PrOH, but with poor overall results (Gook et al., 1993; Todorow et al., 1989). Todorow et al. (1989) reported survival and fertilization rates of 63% and 27%, respectively. When PrOH was used in combination with DMSO, survival and fertilization rates increased to 87% and 42%, respectively. Numerous studies have reported survival and fertilization rates of up to 79% and 50%, respectively, for mouse oocytes cryopreserved using DMSO (Glenister et al., 1987; George and Johnson, 1993; Carroll et al., 1989; Todorow et al., 1989; Schroeder et al., 1990; Aigner et al., 1992; Bouquet et al., 1992). Although one laboratory has reported survival rates of up to 91%, fertilization up to 78%, and blastocyst formation as high as 54.4% (Carroll et al., 1993), it remains to be seen whether their results can be easily reproduced.

SUMMARY OF THE INVENTION

The present invention provides an improved culture and cryopreservation medium which allows an oocyte to remain vital through a freeze/thaw cycle, as well as providing improved cryopreservation for other cell types. The cryopreservation solution according to the present invention employs an improved base-medium composition used for cryopreserving embryos, and has made possible the storage of oocytes from several taxonomically diverse species, as well as the improved storage of embryos.

The long term storage of oocytes and/or ovaries is desired for women undergoing chemo- or radio-therapy for the treatment of cancers, bone marrow transplantations, or other procedures, or even aging, that have the potential to leave the individual sterile. This would allow for the possibility of restored fertility after completion of such procedures, by a process including oocyte retrieval or surgical removal of a portion of the ovary or the whole ovary, cryopreservation in a reduced sodium cryopreservation medium, followed by surgical implantation of the cryopreserved tissue or fertilized oocyte. As stated above, cryopreservation and transplantation of ovarian autografts, using simple embryo freezing protocols, have been successful in mice and sheep (Gosden et al., 1994; Gunasena et al., 1997). Storage of ovarian slices may be improved in a process employing the reduced sodium cryopreservation media according to the present invention, since a greater proportion of oocytes frozen in the present cryopreservation media survive and develop, compared to conventional sodium-based media. This same type of technique may also be used for the cryopreservation of other tissues and organs, for later transplantation or implantation.

To significantly improve oocyte freezing and enable its routine use, the present invention provides a cryopreservation media which, in part, alleviates the damaging effects of sodium transport across cell membranes and/or sodium loading of the cell. Because of the disruptive effects of ions, particularly sodium ions during cell freezing, the present invention seeks to substitute another ion. The preferred major cation in the cell medium according to the present invention is choline. Toner et al. (1993) investigating whether cryoprotectants were absolutely necessary for cryopreservation, reported that mouse zygotes lysed upon warming to room temperature after being cooled to −40° C. in a hypertonic sodium chloride (NaCl)-supplemented phosphate buffered saline (PBS) solution lacking cryoprotectants. In contrast, the majority of zygotes cooled to −40° C. in a hypertonic choline chloride (ChCl)-supplemented PBS solution lacking cryoprotectants, remained intact after warming to room temperature. While the membranes remained intact, these zygotes did not develop normally, indicating that while the ChCl prevented lysis, it was not sufficient to promote development. This study did not seek to address whether the ChCl might be used to replace NaCl or the effect of a mixture of ChCl and cryoprotectant.

The present invention relies on the elimination of NaCl to prevent membrane damage, whereas membrane lysis frequently occurred in cryopreservation medium that was supplemented with NaCl. A preferred substituting composition is ChCl. The present invention therefore eliminates most of the sodium from the cryopreservation medium composition, and replaces it with choline or another suitable cationic species. Choline is the common name for 2-trimethyl amino 1-ethanol, a quaternary amine, and therefore is accompanied by a counterion. Choline is involved with membrane chemistry (e.g., phosphatidyl choline) and intercellular (neurotransmitter acetyl choline) communication. While a direct relation between the cryopreservation solution according to the present invention and these biochemical pathways is not yet understood, the cryopreservation effect may be related. Therefore, compounds which interact or substitute for choline in these pathways may also be useful according to the present invention. The relatively large effective (hydrated) ionic size and low diffusion rate through the cell membrane of choline are believed to be important characteristics. Therefore, other quaternary amines or molecules positively charged at physiological pH may also be useful as cryopreservation solution components.

Thus, the present invention provides a relatively large hydrated diameter organic cation species, preferably choline, as the major extracellular cation, with extracellular sodium reduced to low levels.

The inventor has investigated the effects of choline ions, sodium ions, as well as sucrose, serum, and various cryoprotectants on the ability of mouse oocytes to survive freezing and develop following insemination. The resulting composition was tested as a cryopreservation solution for oocytes of various species. A similar medium containing a low sodium ion concentration was also found suitable for oocyte and embryo culture, thereby avoiding potential loss of oocytes during medium transfer. In this case, choline replaced the majority of sodium in the medium. For oocyte culture, the continued presence of some sodium may be important, e.g., preferably about 10–50 mM. Therefore, the NaCl component of a cryopreservation medium is replaced with ChCl, allowing other sources of sodium ion to remain.

Therefore, the cryopreservation solution according to the present invention preferably has less than 50 mM sodium, and more preferably less than 25 mM sodium, and most preferably less than 10 mM sodium. One embodiment has, for example, a sodium concentration of 16.38 mM (from sodium phosphate buffer), and provides the advantages set forth herein.

The present invention therefore provides a culture medium and cryopreservation solution having a low sodium concentration and providing choline as an cation species. While one embodiment according to the present invention provides low sodium concentrations, it is also possible to replace all of the sodium, for example with potassium, for example by substituting $Na_2HPO_4$ with $K_2HPO_4$. Sodium pyruvate, an optional additive, may also be avoided in the formula. This would leave only trace amounts of sodium ions found in the water used to make the medium.

The concentration of ChCl in the cryopreservation solution composition may also be increased from about 0.137 M to about 0.5 M. This would in effect dehydrate the preserved cell more and help reduce the chance of IIF from occurring.

Because of the relation of cryopreservation solution to the culture medium, according to the present invention, the medium need not be changed or replaced during various phases of cellular manipulation, allowing thawing and stabilization of the cells in the same medium, before changing to a sodium-based medium, as would likely be performed for fertilization. The culture medium may also be modified or altered, e.g., by the addition of sodium-containing medium, or the like.

The ChCl-based culture medium may also be used in other circumstances not involving cryopreservation, where a reduced sodium medium is desired.

Testing on more than 2000 mouse oocytes has shown that most of the mortality occurring when mouse oocytes are cryopreserved is related to cellular disruption by sodium ions. The conventional sodium-based freezing medium was found to be detrimental to oocyte survival, fertilization, and subsequent development in part because of sodium toxicity. According to the present invention, the nonpermeable ionic molecule choline, can substitute for sodium thereby maintaining membrane integrity after oocytes are thawed. Furthermore, the majority of oocytes frozen in ChCl-based medium survive cryopreservation, fertilize, and cleave to peri-implantation stages in vitro. In mouse oocytes, a high degree of survival (85%, n=>2000) was observed, as well as fertilization, and development for mouse oocytes using a simple freezing protocol. Following embryo transfer to pseudopregnant murine dams, blastocysts derived from cryopreserved oocytes are capable of implanting into a receptive uterus and developing to term. These data represent a highly significant improvement in the ability to cryopreserve mouse oocytes. This advancement was made possible by an improvement in cryopreservation medium composition, specifically the removal of NaCl and its replacement with ChCl. This technology has allowed mouse oocytes to be easily and reproducibly frozen and has applications for the storage of oocytes from other species, as well as other cells including embryos, sperm, erythrocytes, and tissues. A cryopreservation solution according to the present invention therefore provides an environment which assures a high degree of survival, fertilization, and development for oocytes.

A dramatic increase in oocyte survival rates was seen when NaCl was replaced with ChCl. Although some sodium is believed to be required for normal cellular functioning, it apparently is not required for cell storage and its absence during the freeze thaw cycle is not detrimental to cellular function after thawing. The survival of mouse oocytes was inversely proportional to the amount of sodium in the freezing medium. As the sodium concentration in the freezing medium decreased, not only did oocyte membrane integrity increase, but cytoplasmic organization, as determined by visual analysis, was more similar to oocytes before cryopreservation. Although oocytes frozen in medium containing 140 mM NaCl remained intact upon thawing, their cytoplasmic organization was different than nonfrozen oocytes, and their ability to fertilize and develop to the blastocyst stage was compromised. In several instances, survival rates of up to 80% were observed when oocytes were frozen in a sodium-based medium, but the majority of these eggs failed to fertilize even though they were frozen and thawed in the presence of serum. These results suggest that even though some degree of membrane intactness can be obtained, intracellular damage has occurred to such an extent that few eggs fertilize and develop.

Studies show that a low NaCl-based culture medium is not toxic to cells, and embryo survival was observed after incubation in a ChCl-based culture medium with about 20 mM sodium ion concentration for about 48 hours.

The presence of either 0.1 or 0.2 M sucrose in the freezing medium did not effect oocyte survival after thawing, but oocytes frozen with 0.2 M sucrose exhibited significantly lower fertilization rates, as compared to those frozen with 0.1 M sucrose.

Although several studies report that the presence of 10–20% fetal bovine serum (FBS) in the freezing and thawing medium improves fertilization rates (Carroll et al., 1993; George and Johnson, 1993; Schroeder et al., 1990), they did improve with the addition of 5–20% FBS to a choline-based cryopreservation medium. However, fertilization rates for frozen oocytes were significantly improved when partial zona dissection was performed prior to insemination. Fertilization rates for nonfrozen control oocytes and frozen partial zona dissected oocytes were similar about 80% each, suggesting that modifications in the zona occurred even in the presence of FBS and that these oocytes could develop normally. Fertilization rates increased to around control levels when partial zona dissection was done on frozen/thawed oocytes. The exact modifications that occur in the zona during cryopreservation have yet to be determined, but some degree of zona hardening does occur. In contrast, almost all partial zona dissected control oocytes fertilize and cleave to the 2-cell stage, indicating that some damage or alteration in the cell membrane occurs in the cryopreserved oocytes. Whether the zona alteration is related to the actual cryopreservation process or to the culture at room temperature during the prefreeze and thaw has yet to be elucidated.

It is therefore an object of the invention to provide a medium for storing cells, comprising a composition, which when constituted in aqueous solution includes less than about 100 mM, preferably less than 50 mM, more preferably less than 25 mM and most preferably less than 20 mM sodium ions, and may be essentially sodium free, and a cellular membrane impermeable organic cation, having an osmolality of between about 250 and 500 mOsm, exclusive of non-ionic and protein solutes. The medium is preferably adapted for use as a cryoperservation solution for cells, the cells being preferably oocytes, and more preferably mammalian oocytes. The solution may also serve as a culture medium for cells, e.g., embryos and, for example, avoids the need to change the base-medium after freezing the cells.

It is another object according to the present invention to provide a medium for storing cells having a low sodium ion concentration, with a cellular membrane impermeable organic cation comprising an organic charged amine, which is preferably choline. The choline is preferably present in an amount greater than 10 mM, more preferably greater than 100 mM, and may be, for example about 137 mM in an isotonic solution, or at least 250 mM and preferably between about 350–500 mM in a hypertonic solution. The choline to sodium ion ratio of the solution is preferably greater than about 0.5:1.

It is a further object of the invention to provide a medium for storing cells having a low sodium concentration, and an osmolality of between about 250 to about 305 mOsm, exclusive of non-ionic and protein solutes. The medium may include, for example, a cryoprotectant, sucrose, e.g., present in an amount of 50–250 mM, and preferably 100 mM, a natural or artificial serum protein, for example fetal bovine serum, e.g., present in an amount of about 5–20%, and may be selected from one or more of the group consisting of fetal bovine serum, newborn calf serum, bovine serum albumin, human serum albumin, human cord serum, and plasminate, and consisting of a phosphate buffer. The cryoprotectant is preferably present in an amount effective to inhibit crystallization of water when frozen, and may be selected from one or more of the group consisting of 1,2 propanediol, dimethyl sulfoxide, glycerol, and ethylene glycol, and for example consists of 100–2500 mM 1,2 propanediol.

It is a still further object according to the present invention to provide a cryopreservation solution preferably having an osmolality of at least about 250 mOsm, and preferably less than about 500 mOsm. A preferred cryopreservation solution has an osmolality of about 275–295 mOsm. The osmolality referred to herein includes ionic constituents, and does not include proteins, cryoprotectant, and sucrose.

It is another object of the present invention to provide a concentrate or powder encompassing the teachings of the present invention, as well as a method of employing the cryopreservation solution to freeze cells, particularly mammalian oocytes.

It is a further object according to the present invention to provide a cryopreservation solution comprising at least 100 mM choline, at least 250 mM 1,2 propanediol and less than about 50 mM sodium.

These and further objects will become apparent from a review of the detailed description of the preferred embodiments.

DETAILED DESCRIPTION OF THE PREFERRED EMBODIMENTS

EXAMPLE 1

A cryopreservation solution was prepared with the composition shown in Table 1, diluted with 18 mOhm distilled water to make 1 liter.

TABLE 1

CRYOPRESERVATION SOLUTION

| Chemical | mM | g/l |
|---|---|---|
| KCl | 2.68 | 0.200 |
| $KH_2PO_4$ | 1.47 | 0.200 |
| $Na_2HPO_4$ (Anhydrous) | 8.03 | 1.140 |
| $MgCl_2$ (Anhydrous) | 0.50 | 0.047 |
| $C_5H_{14}NOCl$ (ChCl) | 136.82 | 19.100 |
| $CaCl_2$ (Anhydrous) | 0.01 | 0.010 |
| D-Glucose | 0.55 | 1.00 |
| Kanamycin Sulfate | 0.04 | 0.025 |
| Phenol Red | 0.01 | 0.005 |

EXAMPLE 2

Collection and Culture of Oocytes

Follicular activity was stimulated in 5–8 week old female C57BL/6×SJL F1 and C57BL/6 mice (Jackson Laboratories, Bar Harbor, Me.) by intraperitoneal injection of 10 IU equine chorionic gonadotropin (Sigma Chemical Co., St. Louis, Mo.), followed 48 h later with 10 IU hCG (Sigma). Cumulus masses were collected from oviducts 13 h post-hCG and treated with 120 U/ml hyaluronidase (Sigma) for 10 min to remove cumulus cells. The oocytes were washed in FHM (Specialty Media; Lavallette, N.J.) and held at RT until cryopreservation or fertilization. All embryo culture was carried out in a 5% $CO_2$ incubator at 37° C., using microdrops (30–50 microliters) of KSOM on Nunc dishes (VWR Scientific; Piscataway, N.J.) flooded with M2 twice-washed mineral oil (Squibb; Park Avenue Chemists Ltd.; New York, N.Y.).

Oocyte Freezing and Thawing

Oocytes that were translucent, round, having extruded the first polar body, and appeared normal, were selected for cryopreservation. Several of these oocytes were set aside to be used as nonfrozen controls. Oocytes were cryopreserved in a newly-formulated modified PB1 medium according to the present invention, having a composition as shown in Table 1. Oocytes were pre-equilibrated at 23° C. in the Cryopreservation solution according to the present invention containing 1.5 M cryoprotectant for 10 min and then transferred to Cryopreservation solution according to the present invention containing 1.5 M cryoprotectant and 0.1 or 0.2 M sucrose for 2 to 20 min. During this time the oocytes were loaded into 0.25 ml French straws (IMV International; Minneapolis, Minn.) and heat sealed at both ends. The straws were placed in a BioCool III programmable freezer (FTS systems; Stone Ridge, N.Y.), cooled at a rate of 2° C./min to −7° C., seeded using forceps cooled in $LN_2$, held at −7° C. for 10 min, and cooled at a rate of −0.3° C./min to −33° C. before plunging into $LN_2$. Oocytes were thawed by exposing the straw to air for 10–30 sec before immersing in a 30° C. water bath for an additional 10 sec. The oocytes were rinsed through a series of eight drops of 23° C. medium at 5 min intervals in order to remove the cryoprotectant and sucrose. Thawed oocytes were transferred stepwise into 1) Cryopreservation solution according to the present invention containing 0.2 M sucrose and 1.0 M cryoprotectant, 2) Cryopreservation solution according to the present invention containing 0.2 M sucrose and 0.5 M cryoprotectant, 3) Cryopreservation solution according to the present invention containing 0.2 M sucrose, 4) Cryopreservation solution according to the present invention containing 0.1 M sucrose, 5) Cryopreservation solution according to the present invention, and 6) mCZB (Chatot et al., 1989; Kimura and Yanagimachi, 1995). The freezing and step-out solutions were supplemented with 0, 5, 10, 15 or 20% FBS (Gibco BRL; Gaithersburg, Md.).

Fertilization and Embryo Culture

Spermatozoa from male CB6 or B6SJL mice, 3 to 9 months old, were released by epididymal puncture into equilibrated Ham's F10 medium (Sigma) supplemented with 4 mg/ml BSA (Sigma). The sperm were allowed to capacitate for 1 to 2 h before being used for insemination. Fresh and cryopreserved oocytes were cultured in Ham's F10 medium containing approximately $5 \times 10^5$ motile sperm for 5 to 9 h, washed through three drops of equilibrated KSOM, and cultured in KSOM for 2 days, at which point they were moved to a fresh drop KSOM for an additional 3 days. Partial zona dissection (PZD) was performed on thawed oocytes before insemination to aid fertilization, as well as nonfrozen oocytes to serve as controls. We also inseminated several groups of control and thawed oocytes without performing PZD. Oocytes were examined for fertilization by the presence of 2 pronuclei, 2 polar bodies, or two uniform blastomeres 20 h after insemination. The resulting embryos were examined daily for the extent of developmental progression. Some of the embryos reaching the morulae or blastocyst stage were selected for use in embryo transfer experiments.

Embryo Transfer

Recipient CD1 female mice were paired with vasectomized CB6 males to induce a state of pseudopregnancy. Females were checked daily for a vaginal plug, indicating that mating had occurred and that the female was in Day 1 of pseudopregnancy. After inducing a surgical plane of anesthesia by i.p. injection of 0.16 mg/g of 2.5% avertin (Hogan et al., 1994), Day 3 pseudopregnant female mice were placed on their abdomen and a 7 mm dorsal incision was made above the sacral vertebrae, 3 cm from the base of the tail. The skin was pulled to the side and a 3 mm incision was made in the peritoneum dorsal to the ovary. The uterus was retracted and 3–7 cryopreserved or control embryos were injected into the upper third of the uterine horn using a glass micropipette inserted through a hole made with a 25 gauge needle. Care was taken to avoid expelling air and excess medium into the uterus. The procedure was then repeated on the contralateral uterine horn and the skin was closed using a wound clip. Following each transfer, the micropipette was expressed into a dish of medium to determine the number of embryos not delivered.

Examination of Implantation Sites and Live Offspring

On gestation Day 10 or 18, embryo recipients were sacrificed by cervical dislocation, their uteri were removed, and all fetal material removed through antimesometrial incisions made in the uterine horns. Day 10 fully-formed fetuses and resorbed fetuses were recorded. Day 18 fetuses were visually examined for gross morphological abnormalities. Day 18 uterine horns were stained with 10% ammonium sulfide for 24 h to reveal the implantation sites as black spots for counting.

EXAMPLE 3

Metaphase II oocytes from mouse, cat, bovine, and human were cryopreserved using cryopreservation solution supplemented with 1,2-propanediol. Oocytes were thawed at a later date and the number of intact oocytes after thawing as well as their development following insemination (only mouse, human, and cat oocytes were inseminated) were recorded. These initial studies test the functionality of Cryopreservation solution according to the present invention as an effective cryopreservation medium.

Mouse Experiments

Mouse oocytes (n=1380) were cryopreserved on using Cryopreservation solution according to the present invention supplemented with 1.5 M propanediol (PrOH) and subsequently thawed.

TABLE 2A

| | |
|---|---|
| Survival (n/%): | 1276/97.6 |
| Fertilized (%): | 71.7 |
| Developed to Blastocyst (%): | 51.9 |
| Embryos Replaced (n): | 122 |
| Embryos Implanted (n): | 24 |
| Viable Fetuses (n): | 3 |

Human Experiments

Human oocytes (n=10) were cryopreserved using Cryopreservation solution according to the present invention supplemented with 1.5 M PrOH and subsequently thawed.

TABLE 2B

| | |
|---|---|
| Survival (n/%): | 10/100 |
| Fertilized (n/%): | 9/90 |

Cat Experiments

Domestic cat oocytes (n=201) were cryopreserved using Cryopreservation solution according to the present invention supplemented with 1.5 M PrOH and subsequently thawed.

TABLE 2C

| | |
|---|---|
| Survival (n/%): | 153/76.1 |
| Fertilized (n): | 10 |

Bovine Experiments

Bovine oocytes (n=211) were cryopreserved using Cryopreservation solution according to the present invention supplemented with 1.5 M PROH and subsequently thawed.

TABLE 2D

| | |
|---|---|
| Survival (n/%): | 87/41.2 |

These studies show that eggs from various species can remain intact, and for mouse oocytes, fertilize, develop in vitro, and implant and go to full term after freezing in a cryopreservation solution according to the present invention.

EXAMPLE 4

Effect of Altering the Sodium Concentration in the Cryopreservation Medium

The effect of altering the sodium concentration in the freezing medium on oocyte survival, fertilization, and development after cryopreservation was examined. A NaCl-based freezing medium (ETFM; Gibco BRL, Grand Island, N.Y.) was modified by substituting an equal molar amount of NaCl with 0, 0.0137, 0.137, 0.2, or 0.5 M ChCl (Table 3). At concentrations equal to or greater than 0.137 M ChCl, NaCl was absent from the medium. This newly formulated cryopreservation medium, containing ChCl and no NaCl, provides significant benefits according to the present invention. The effect of removing all the sodium (<2.0 mM; approximate final concentration) from the freezing medium by substituting an equal molar amount of NaCl with ChCl and $Na_2HPO_4$ with $K_2HPO_4$ was also examined.

TABLE 3

Effect of the Concentration of Sodium Ions and Choline Ions in the Freezing Medium on Oocyte Cryopreservation

| | Choline/Sodium (mM)* | | | | | |
|---|---|---|---|---|---|---|
| Number of Oocytes | 0/145 | 13.7/131.3 | 137/8 | 200/8 | 500/8 | 137/0 |
| Recovered | 29 | 40 | 1308 | 46 | 35 | 23 |
| Survived (%) | 24 (82.7) | 27 (67.5) | 1276 (97.6) | 44 (95.6) | 34 (97.1) | 23 (100) |
| End of Step-Out (%) | 8 (27.6) | 14 (35.0) | 982 (75.0) | 42 (91.3) | 34 (97.1) | 20 (87) |
| Inseminated | 6 | 14 | 930 | NA | NA | 20 |
| 2-Cell | 4 | 4 | 667 | NA | NA | 17 |
| Morula | 4 | 4 | 554 | NA | NA | 15 |
| Blastocyst | 4 | 3 | 483 | NA | NA | 14 |

*Concentration of choline ions and sodium ions in the freezing medium.
NA: not assessed.

A dramatic and significant increase in oocyte survival, fertilization, and development rates were observed when NaCl was replaced with ChCl, as shown in Table 3. There was no difference (P>0.05) in oocyte survival, fertilization, and developmental rates when the freezing medium contained NaCl or 0.0137 M ChCl. In contrast, when the NaCl in the freezing medium was replaced with 0.137, 0.2, or 0.5 M ChCl, survival, fertilization, and blastocyst development rates were, on average, more than doubled (p<0.05). To further investigate the impact of sodium on oocyte survival following cryopreservation, freezing medium was made without sodium by replacing NaCl with ChCl and $Na_2HPO_4$ with $K_2HPO_4$. When oocytes were frozen with this medium, 80% survived following thawing and 60% of all oocytes frozen, fertilized and developed to the blastocyst stage, as shown in Table 3. These results were similar (p>0.05) to those obtained when oocytes were frozen in freezing medium containing $Na_2HPO_4$ and lacking NaCl, and greater (p<0.05) when compared with oocytes frozen in NaCl containing medium.

EXAMPLE 5

Effect of Sucrose on Oocyte Cryopreservation

The ability of sucrose to act as a nonpermeating and osmotically active compound has beneficial effects on embryo survival when used in conjunction with other cryopreservatives including 1,2-propanediol (PrOH) and dimethyl sulfoxide (DMSO; Friedler et al., 1988; Lassalle et al., 1985). In spite of its beneficial effects, preimplantation embryos exposed for long periods of time or to high concentrations of sucrose, show reduced developmental potential (Renard et al., 1984). We therefore examined survival, fertilization, and development of oocytes frozen in either 0.1 M or 0.2 M sucrose.

The concentration of sucrose in the freezing medium had no significant effect on oocyte survival through the thaw. In contrast, oocytes frozen in 0.1 M sucrose fertilized at a higher rate (p<0.05), than oocytes frozen in 0.2 M sucrose. Following fertilization and cleavage to the 2-cell stage, development to blastocyst was not different between the two groups (p>0.05).

EXAMPLE 6

Effect of Serum on Oocyte Cryopreservation

Hardening of the zonae pellucidae due to the premature release of cortical granules occurs during mouse oocyte thawing and inhibits subsequent fertilization (Vincent et al., 1990; Glenister et al., 1987; Carroll et al., 1989, 1990). Zona hardening has been shown to be reduced or prevented when fetal bovine serum (FBS) was included both in the freezing and thawing media (Schroeder et al., 1990; Carroll et al., 1993). It is therefore important to determine the effect of FBS on oocyte survival and their ability to be fertilized after cryopreservation. For this study, Cryopreselvation solution according to the present invention was supplemented with 0%, 5%, or 10% FBS for use in both the freezing and thawing procedures. 10% FBS is preferred.

EXAMPLE 7

Effect of Cryoprotectant Type on Oocyte Cryopreservation

All commonly used cryoprotectants used for the storage of embryos and sperm such as PrOH, DMSO, glycerol, and ethylene glycol are toxic to cells. Common embryo freezing protocols use 1 to 2 M PrOH, DMSO, glycerol, or ethylene glycol (Shaw et al., 1995; Lassalle et al., 1985; Willadsen, 1977; Kasai et al., 1981). The toxicity of these cryopreservatives varies with concentration and exposure time; at lower concentrations and shorter exposure times, the less toxic they are to embryo development (for review see Friedler et al., 1988). The ability of mouse oocytes to survive freezing was examined using 0.375, 0.75, and 1.5 M PrOH, as well as 1.5 M DMSO. The results are summarized in Tables 4 and 5.

TABLE 4

Effect of PrOH Concentration on Oocyte Cryopreservation.

| [PrOH] | Recovered | Survived (%) | End of Step-Out (%) |
|---|---|---|---|
| 1.5 M | 1597 | 1568 (98.2) | 1247 (78.1) |
| 0.75 M | 87 | 87 (100) | 77 (88.5) |
| 0.375 M | 58 | 41 (70.7) | 8 (13.8) |

TABLE 5

Effect of Different Cryoprotectants on Oocyte Survival, Fertilization, and Development.

| | Cryoprotectant | |
|---|---|---|
| Number of Oocytes | PrOH 1.5 M | DMSO 1.5 M |
| Recovered | 1308 | 113 |
| Survived (%) | 1276 (97.6) | 105 (92.9) |
| End of Step-Out (%) | 982 (75.0) | 96 (85.0) |
| Inseminated | 930 | 76 |
| 2-Cell | 667 | 62 (81.6) |
| Morula | 554 | 56 (73.7) |
| Blastocyst | 483 | 48 (63.2) |

The type of cryoprotectant and the concentration used effected oocyte survival, fertilization, and development. A greater (p<0.05) percentage of oocytes frozen in 1.5 or 0.75 M PrOH remained intact throughout the thaw procedure as compared to oocytes frozen in 0.375 M PrOH.

There has thus been shown and described a cell culture medium and cryopreservation solution which fulfills all the objects and advantages sought therefor. Many changes, modifications, variations and other uses and applications of the subject invention, will, however, become apparent to those skilled in the art after considering this specification and the accompanying drawings which disclose the preferred embodiment thereof. All such changes, modifications, variations and other uses and applications which do not depart from the spirit and scope of the invention are deemed to be covered by the invention, which is limited only by the claims which follow.

REFERENCES

Hogan, B., Beddington, R., Constantini, F., and Lacy, E. (1994). Manipulating the mouse embryo, 2 Edition (Plainview: Cold Spring Harbor Laboratory Press).

What is claimed is:

1. A medium for storing cells, comprising a composition, which when constituted in aqueous solution includes less than about 50 mM sodium ions and choline salt being present at a concentration of at least 100 mM, and a cryoprotectant present in an amount effective to reduce intracellular ice formation during freezing of the cells.

2. The medium according to claim 1, adapted for use as a cryopreservation solution for mammalian cells.

3. The medium according to claim 1, adapted for use as a cryopreservation solution for mammalian oocytes.

4. The medium according to claim 1, adapted for use as a culture medium for mammalian cells.

5. The medium according to claim 1, adapted for use as a culture medium for mammalian oocytes.

6. The medium according to claim 1, adapted for use as an insemination medium for mammalian oocytes.

7. The medium according to claim 1, comprising about 137 mM choline when constituted.

8. The medium according to claim 1, comprising at least 250 mM choline when constituted.

9. The medium according to claim 1, comprising between about 350 to about 500 mM choline when constituted.

10. The medium according to claim 1, comprising less than about 25 mM sodium when constituted.

11. The medium according to claim 1, comprising less than about 20 mM sodium when constituted.

12. The medium according to claim 1, comprising less than 2 mM sodium ion when constituted.

13. The medium according to claim 1, comprising a solution having an osmolality of between about 250 to about 305 mOsm, exclusive of osmolality attributable to non-ionic and protein solutes.

14. The medium according to claim 1, wherein said cryoprotectant is selected from one or more of the group consisting of 1,2 propanediol, dimethyl sulfoxide, glycerol and ethylene glycol.

15. The medium according to claim 1, further comprising a phosphate buffer.

16. The medium according to claim 1, wherein a molar ratio of choline to sodium is greater than about 2:1.

17. The medium according to claim 1, wherein a molar ratio of choline to sodium is greater than about 5:1.

18. The medium according to claim 1, wherein a molar ratio of choline to sodium is greater than about 10:1.

19. The medium according to claim 1, adapted for use as a cryopreservation solution for embryos.

20. A method for using the medium according to claim 1, comprising the steps of:

placing a cell in the medium; and freezing the medium containing the cell.

21. The medium according to claim 2, further comprising sucrose.

22. The medium according to claim 2, further comprising between about 50 mM and 250 mM sucrose.

23. The medium according to claim 2, further comprising about 100 mM sucrose.

24. The medium according to claim 2, further comprising sucrose in an effective amount to reduce freeze-mediated cell damage, wherein sufficient cryoprotectant permeates the cell to impede intracellular ice formation.

25. The medium according to claim 2, further comprising effective amounts of a cryoprotectant, and sucrose, respectively, to reduce freeze-mediated cell damage, and a serum protein, wherein sufficient cryoprotectant permeates the cell to block intracellular ice formation.

26. The medium according to claim 2, wherein said cryoprotectant comprises at least 250 mM 1,2 propanediol.

27. The medium according to claim 2, wherein said cryoprotectant comprises at least 500 mM 1,2 propanediol.

28. The medium according to claim 2, wherein the cryoprotectant comprises at least 1000 mM 1,2 propanediol.

29. The medium according to claim 3, wherein said cryoprotectant comprises at least 250 mM 1,2 propanediol, further comprising sucrose present in an effective amount to reduce freeze-mediated cell damage, and a serum protein.

30. The medium according to claim 2, having a choline to sodium ion molar ratio of greater than about 2:1.

31. The method according to claim 30, wherein the cell is an oocyte.

32. The method according to claim 30, wherein the medium contains at least 137 mM choline.

33. The method according to claim 30, wherein the medium contains between about 250 mM and 500 mM choline.

34. The method according to claim 30, wherein the medium comprises less than 25 mM sodium.

35. The method according to claim 30, wherein the medium is substantially free of soluble sodium ion.

36. The method according to claim 30, wherein the cryoprotectant is selected from one or more of the group consisting of 1,2 propanediol, dimethyl sulfoxide, glycerol and ethylene glycol.

37. The method according to claim 30, wherein the medium further comprises between about 50 mM and 250 mM sucrose.

38. The method according to claim 30, wherein the medium comprises a soluble protein.

39. The method according to claim 30, further comprising the step of thawing the medium containing the cell.

40. The method according to claim 31, wherein the cell is a mammalian oocyte, further comprising the step of fertilizing the oocyte after thawing.

41. The method according to claim 40, further comprising the step of culturing the fertilized oocyte as an embryo.

42. The method according to claim 40, further comprising the step of replacing the oocyte, after fertilization, in an oviduct or uterus.

43. A method of using the medium according to claim 1, for cryopreservation of a cell, comprising the steps of:

(a) providing a cell in an extracellular medium having a sodium ion osmolality of at least 50 mOsm;

(b) exchanging the extracellular medium to the medium of claim 1;

(c) reducing an intercellular hydration below physiological levels; and (d) reducing a temperature of the cell in the changed extracellular medium to cryopreserve the cell.

44. An aqueous medium having a mammalian cell therein, comprising a cryoprotectant in an effective amount to reduce intercellular ice formation, less than about 25 mM sodium ions, and at least 100 mM choline salt.

45. The medium according to claim 44, comprising about 137 mM choline when constituted.

46. The medium according to claim 44, comprising at least 250 mM choline when constituted.

47. The medium according to claim 44, comprising between about 350 to about 500 mM choline when constituted.

48. The medium according to claim 44, comprising less than about 2 mM sodium ion when constituted.

49. The medium according to claim 44, comprising a solution having an osmolality of between about 250 to about 305 mOsm, exclusive of osmolality attributable to non-ionic and protein solutes.

* * * * *